United States Patent
Rosendahl et al.

[11] Patent Number: 5,769,896
[45] Date of Patent: Jun. 23, 1998

[54] PROSTHETIC FOOT WITH ANKLE

[75] Inventors: Brent L. Rosendahl, Tualatin; Terry L. Creamer, Rainier, both of Oreg.

[73] Assignees: Brent Rosendahl; Terry Creamer, both of Tualatin, Oreg.

[21] Appl. No.: 315,814

[22] Filed: Sep. 30, 1994

[51] Int. Cl.$^6$ .................................................. A61F 2/66
[52] U.S. Cl. .............................. 623/49; 623/52; 623/55
[58] Field of Search .................... 623/55, 53, 47–52, 623/54, 56

[56] References Cited

U.S. PATENT DOCUMENTS

| | | | |
|---|---|---|---|
| 969,196 | 9/1910 | Rowley | 623/49 |
| 1,174,127 | 3/1916 | Davis et al. | 623/52 X |
| 2,731,645 | 1/1956 | Woodall | 623/53 |
| 4,652,266 | 3/1987 | Truesdell | 623/55 |
| 4,892,554 | 1/1990 | Robinson | 623/55 |
| 5,116,384 | 5/1992 | Wilson et al. | 623/49 |

FOREIGN PATENT DOCUMENTS

| | | | |
|---|---|---|---|
| 2653327 | 4/1991 | France | 623/49 |
| 0309817 | 3/1957 | Italy | 623/53 |
| 0391635 | 5/1933 | United Kingdom | 623/53 |
| 0621576 | 4/1949 | United Kingdom | 623/49 |
| 8806431 | 9/1988 | WIPO | 623/53 |
| 9100070 | 1/1991 | WIPO | 623/53 |
| 9220305 | 11/1992 | WIPO | 623/53 |

*Primary Examiner*—David H. Willse

[57] ABSTRACT

An improved prosthetic foot comprising an energy storage keel and a modified ball and socket ankle joint. The foot and ankle are casted as a single unit, from a urethane copolymer. The movement of the ankle joint is controlled by the use of elastic inserts. These inserts are of various durometers and are interchangeable. Modifying the gait characteristics of this invention can be easily accomplished by simply removing and replacing the elastic inserts. These inserts can be installed without any tools or disassembly of the ankle joint. The attachment to a prosthetic limb is accomplished through the use of an attachment bolt; this bolt also serves as a strengthening and stiffening element for the ankle joint. The energy storage keel of this present invention is comprised of a forefoot having an arch and a resilient toe, which absorbs loads as the user walks and returns the absorbed energy consistent with an energy storage and return foot.

3 Claims, 4 Drawing Sheets

PROSTHETIC FOOT WITH ANKLE

BACKGROUND

1. Field of Invention

The invention relates to an artificial foot with ankle, specifically to an energy storage foot having an ankle joint to simulate the natural motion of the human foot.

2. Description of Prior Art

Originally, prosthetic feet were designed without the benefit of ankle motion, such as SACH feet. These ridged ankle feet could not duplicate the smooth gait characteristics of the human foot, thus the user was required to "vault" over the stiff toe segment.

Recent improvements in the field include several different "energy storage" feet such as U.S. Pat. No. 4,547,913 to Phillips, known as the Flex Foot, which have been variations of leaf spring designs. Because these leaf springs are not variable they tend to work well for only one cadence or gait speed. They don't vary with changing conditions. If they are sized appropriately for a walking gait, they may tend to be too flexible for heavier usage such as running or carrying heavy loads and they allow for no ankle rotation.

Various designs have been introduced in recent years to allow near anatomical range of motion, in combination with an "energy storage" feature. These feet give the user a smooth ankle motion and also allow the benefit of energy storage. However, complexity of the designs, costly manufacturing techniques, difficult fitting procedures, high maintenance and expensive materials have limited these designs.

Inventors have incorporated ball and socket joints into foot designs before as shown in U.S. Pat. No. 5,112.356 to Harris. The motion of these ball and socket joints is controlled by some mechanical means, to simulate the control carried out by the bones, muscles, tendons and ligaments of the human foot and leg. These designs have some problems, such as difficulty of adjustment and high maintenance. Because they use a single elastic ring of constant durometer, they cannot be easily adjusted for different durometers anteriorly or posteriorly. The elastic rings used in these designs are relatively small in size and they break down quickly. Also they often require special tools to compress and disassemble the joint to replace these elastic rings, making changes or adjustments difficult and time consuming for the professional, and nearly impossible for the user.

Each of the feet which combine energy storage and ankle rotation heretofore known suffer from a number of disadvantages.

(a) Difficult fitting and adjusting procedures, with many adjustments available to the user the initial set-up and fitting can be very complex and time consuming.

(b) Adjustments often require disassembly of the ankle joint to make changes, and may require special tools and training.

(c) The complexity of these designs make them very difficult for the user to make any of their own adjustments. All known devices in this group utilize joints that are made up of several components that are fastened together, to create either a ball and socket or a clevis joint.

(d) High maintenance. Other inventions having many moving parts and many adjustments require more up-keep and maintenance. Spare parts may need to be purchased or stocked by the fitter, and special tools might need to be purchased.

(e) Complexity of manufacture. Many of the current inventions ate manufactured from carbon fiber composites formed in a wet lay-up molding technique. This process is both complex and expensive.

(f) When in use many of the gait modification parts of the current inventions are internal to the joint; with these designs the user cannot see these parts. They are unable to evaluate their condition, or even confirm which part is being used.

Objects and Advantages of this Invention

The object of this foot/ankle is to provide a design which incorporates an energy storage element in the form of a keel with an arch and toe segment which act as a leaf spring, with a dynamic ankle joint which in turn simulates the natural motion of the human foot in dorsi-flexion and plantar flexion, as well as medial/lateral rotation. The function of the ankle joint will be controlled by the use of elastic inserts which are of various durometers and can be quickly and easily changed.

Accordingly, several objects and advantages of this invention are:

(a) With only one moving part and only five separate parts per complete assembly, and no mechanical adjustments our foot/ankle will be the easiest of its type to fit and to adjust.

(b) The simplicity of our foot/ankle will provide for easy adjustments, as our design is molded as a single unit it cannot be disassembled. No special tools or training will be required.

(c) The use of various durometer interchangeable elastic inserts will allow the user to easily adjust the gait characteristics.

(d) The simplicity of our foot/ankle provides for very little maintenance or repair. The joint in our invention is closed; it is molded or casted as a single unit it cannot be disassembled.

(e) The simplicity of our foot/ankle allows for simple relatively inexpensive manufacturing techniques.

(f) In our foot/ankle the elastic inserts are external to the joint and can be easily inspected. By providing various color coded elastic inserts with our foot/ankle, the user will be able to easily identify which insert is in use and evaluate its condition.

Further objects and advantages of this invention will become apparent from a consideration of the drawings and ensuing descriptions.

Figure 1:
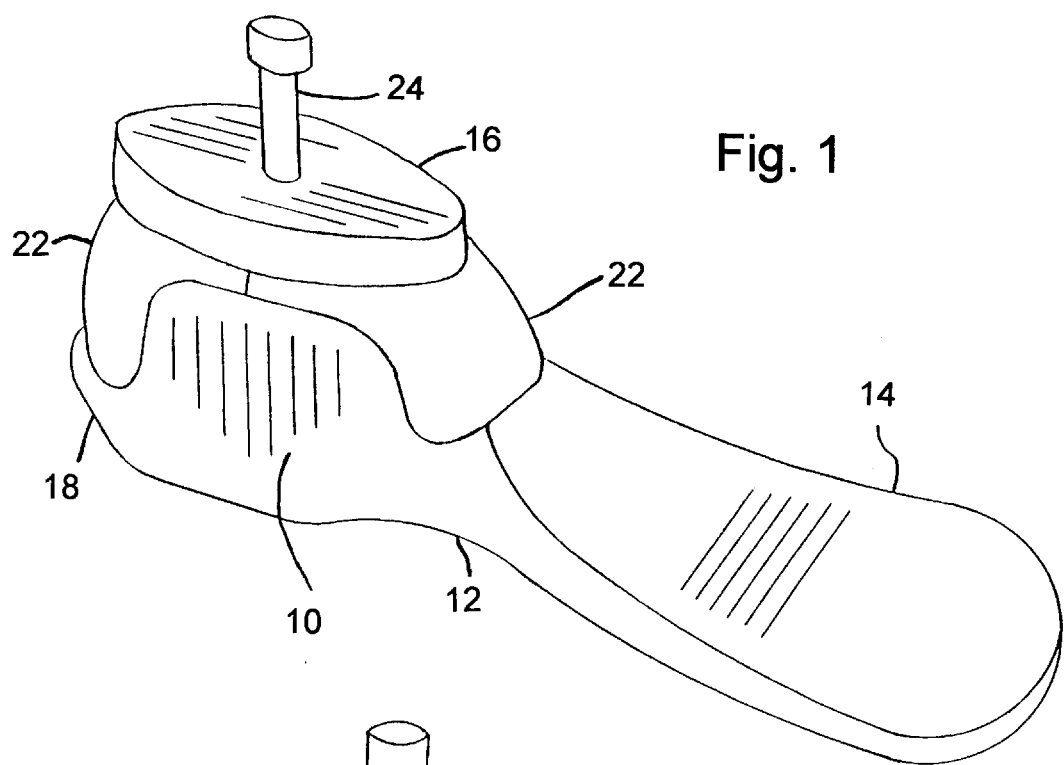
FIG. 1 is a perspective side view showing the foot/ankle with the elastic inserts and the attach bolt in place.

| Reference Numerals In Drawings | | | |
|---|---|---|---|
| 10 | Keel | 22a | Insert Arm |
| 10a | Anterior Cavity | 22b | Insert Lock |
| 10b | Posterior Cavity | 22c | Insert Radius |
| 12 | Arch area | 24 | Attachment Bolt |
| 14 | Toe area | 24a | Threaded shank |
| 16 | Top | 26 | Anterior Cavity Radius |
| 16a | Recess | 28 | Posterior Cavity Radius |
| 18 | Heel | 30 | Collar |
| 20 | Ball | 32 | Cosmetic Foot Shell |
| 20a | Lubrication Hole | 32a | Foot Shell Heel |
| 20b | Threaded Hole | 34 | Socket |
| 22 | Elastic Inserts | | |

DESCRIPTION—FIG. 1 TO 5

FIG. 1 is a perspective side view showing our foot with ankle. A prosthetic foot is designated by the reference number 10 being a keel component containing a ball and socket ankle joint. An arch designated by number 12, a resilient toe designated as 14, a top 16 provides the means for mounting to the prosthetic leg (not shown). A heel 18 is just posterior of the ankle joint. A pair of elastic inserts 22 are interchangeable and of various durometers. An attachment bolt 24 is threaded into the ankle joint to provide a means of attachment to the prosthetic limb (not shown) and also provides for strengthening the ankle joint. Shown in dashed line is a cosmetic cover 32 made of urethane foam.

Figure 2:
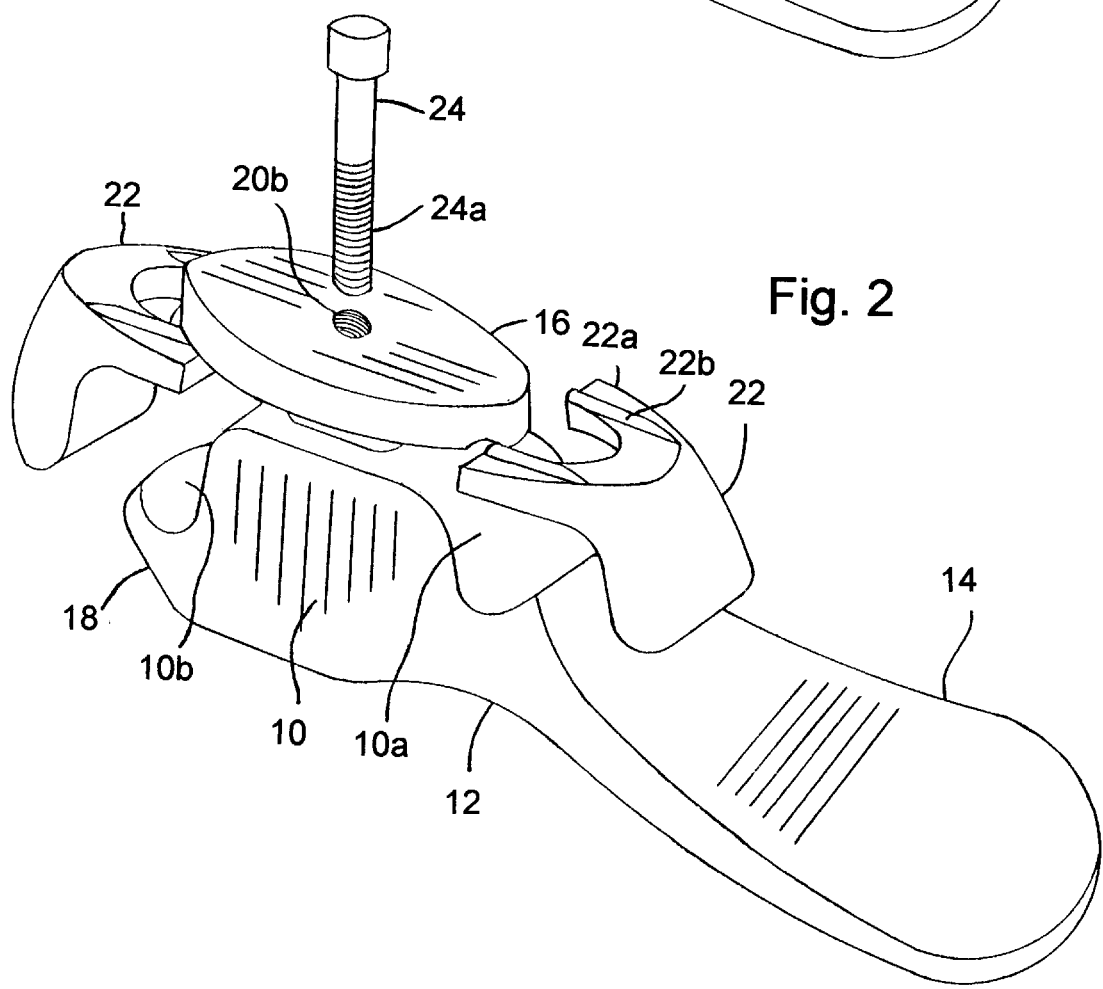
FIG. 2 is an exploded view showing the relationship between the keel, the elastic inserts and the attach bolt.

FIG. 2 is an exploded view showing the relationship of the various components of this foot with ankle. The keel 10 inclusive of the arch 12, toe 14, an anterior cavity 10aZ, a posterior cavity 10b, top 16, a threaded hole 20b, heel 18, an anterior cavity radius 26 and a posterior cavity radius 28 are all molded or casted into one component. The elastic inserts 22 with a bottom radius 22c fits into the cavities 10a and 10b with radii 26 and 28 respectively; an arm 22a with an insert lock 22b slides around the joint, in a space between the keel 10 and the top 16. The attach bolt 24 with a threaded portion 24b, is to be installed into the threaded hole 20b providing a means of attachment to the prosthesis (not shown) and strengthening the joint component.

Figure 3:
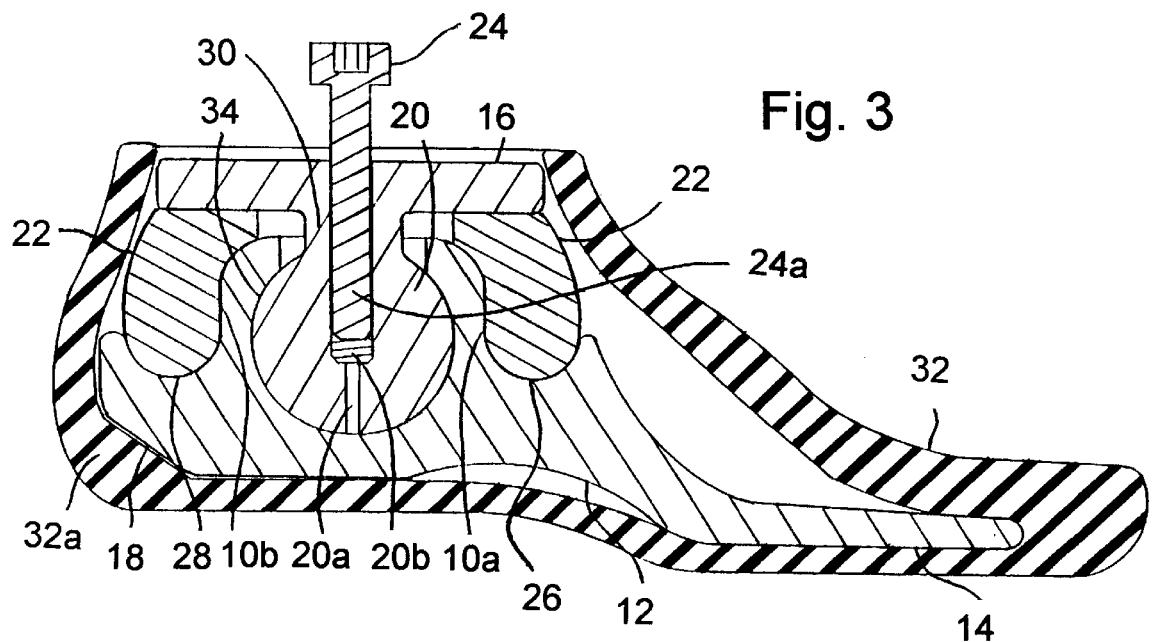
FIG. 3 is a side view cross section showing the ball and socket, the elastic inserts, the attach bolt and cosmetic cover.

Our FIG. 3 represents a side view cross section. The keel 10 as can be seen contains a ball 20 and a socket 34 joint. The ball 20 along with the collar 30, and the top 16, with the internal threaded hole 20b are molded or casted as one part from a urethane copolymer. The socket 34 is formed by molding or casting the same urethane copolymer around the previously formed ball 20. as the keel 10, comprising the arch 12, toe 14, heel 18, anterior insert cavity 26 and posterior insert cavity 28 are being created. The elastic inserts 22 can be seen held in position between the top 16 and their respective cavities 26 and 28. The mount bolt 24 is in position in the threaded hole 20b to act as both a means of attachment to the prosthesis (not shown) and as a structural member adding strength and stiffness to the joint, by passing through the top 16, the collar 30 and into the ball 20. A hole 20a from the bottom of the threaded hole 20b into the socket 34 is a means of introducing lubrication to the ball 20 and socket 34 joint. The cosmetic foot shell 32 provides a means to finish the prosthetic foot. It is fabricated of a resilient urethane foam material which allows it to stretch around the ankle and foot assembly. A heel area 32a is of greater thickness than the surrounding areas.

Figure 4:
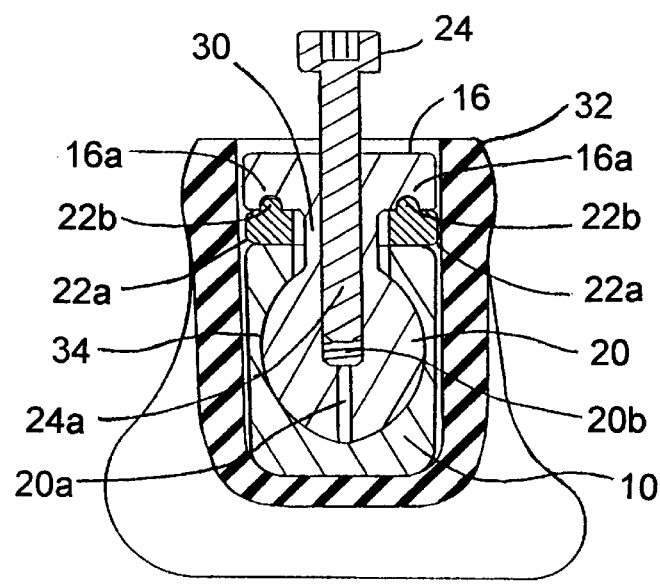
FIG. 4 is a cross sectional view through the elliptical ball and socket, as viewed from the rear.

FIG. 4 is a cross sectional view through the ball and socket joint, as viewed from the rear. The ball 20 can be seen as having an elliptical shape. The relationship of the top 16 with the elastic insert 22 can be seen, the fit of an insert lock 22b with a recess 16a holds the arms 22a in position while in use.

Figure 5A:
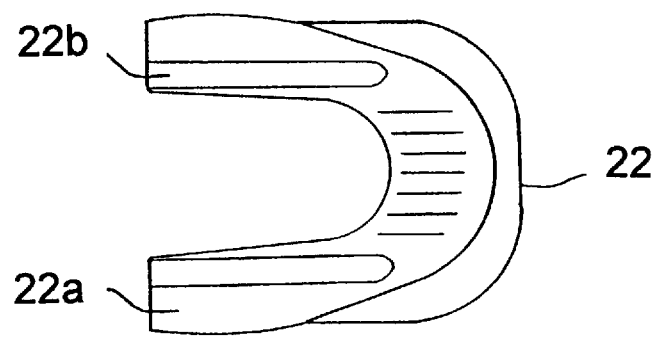
FIGS. 5a–5c are views of the elastic inserts.
Figure 5B:
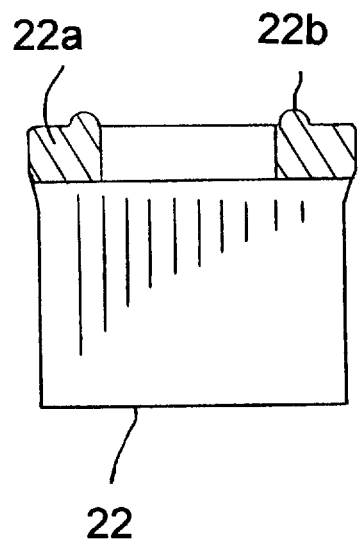

The drawing identified as FIG. 5 represents three views of the elastic inserts 22. View 5a is from the top showing the arms 22a; the purpose of these arms is to wrap around the joint and help hold the insert 22 in place during use.

Our view 5b depicts the elastic insert 22 looking toward the back of the foot, showing an insert lock 22b which works with the corresponding recess 16a on the top part 16(see FIG. 4); this interlocks the top 16 and the elastic insert 22 to keep the arms from slipping out during use.

Figure 5C:
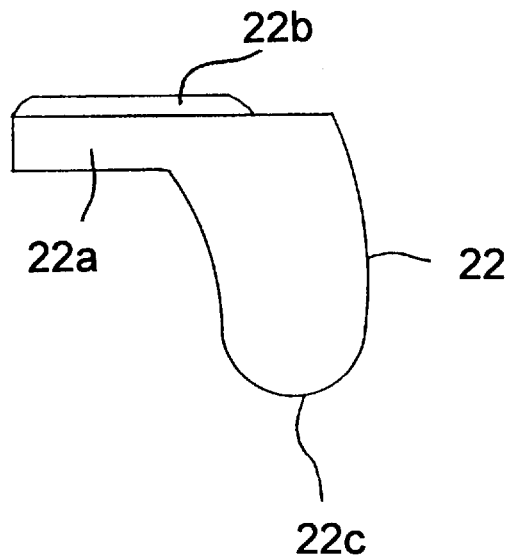

FIG. 5c represents a side view of 22. The insert radius 22c on the bottom portion of the elastic insert 22 works with radii 26 and 28 of keel 10(see FIG. 2) respectively to hold the elastic inserts 22 in position during use.

Operation of the Invention

From FIG. 2, showing an exploded view of our foot/ankle, the assembly of the elastic inserts 22 into the keel 10 can be seen. They are positioned into the cavities 10a and 10b respectively. The arms 22a slip into an area between the keel 10 and the top 16. When both elastic inserts are in place they form an elastic interface of varying thickness and of selectable durometer completely around the ankle joint. The elastic inserts 22 are of various durometer so that gait characteristics can be adjusted by changing from one to another. This is accomplished by hand and no tools or disassembly are required. Referring now to FIG. 4, as can be seen the ball 20 and socket 34 are of an elliptical shape, this will allow free rotation around the lateral axis and restrict but not eliminate rotation about both the longitudinal and vertical axes. The urethane copolymer from which the keel 10 and top 16 are molded or casted, has enough flexibility to allow movement in the longitudinal and vertical axes, which helps simulate the natural rotations of the human foot and ankle. The function of the elastic inserts 22 is to control the rotation about all three axis. The function of the elastic insert 22 in the posterior cavity 10b (see FIG. 3) is to control the speed and degree of rotation in a plantar flexion condition. The function of the elastic insert 22 installed in the anterior cavity 10a is to control the speed and degree of rotation in a dorsi-flexion condition. As can be seen in FIG. 4 the arms 22a fill the space between the keel 10 and the top 16, this adds a resistance to rotation about the longitudinal axis and thus helps control the medial and lateral forces encountered in walking. Further explanation of the operation of our foot/ankle will be evident from the following description of the functions of the various parts and their movements during one step from heel strike through toe off.

Figure 6A:
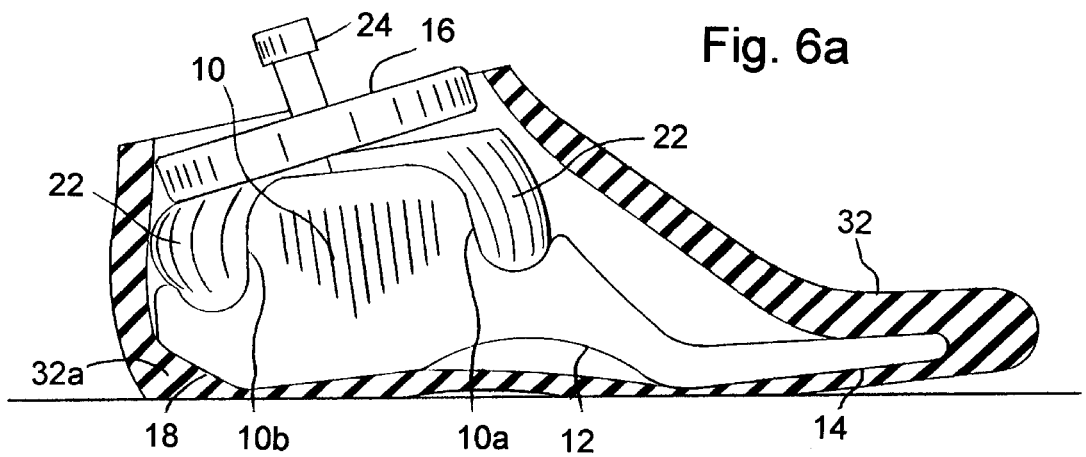
FIG. 6a is a side view showing the rotation of the joint and the compression of the elastic insert in a plantar flexed condition. The cosmetic foot shell is shown in section.

At heel strike the thick portion of the foot shell heel area 32a compresses between the ground and the heel 18. As the heel area becomes completely compressed, the keel 10 inclusive of the arch 12 and the toe 14 rotate against the resistance of the elastic insert 22 compressing it, until a foot flat condition is achieved; the speed and degree of rotation is controlled by the durometer of the elastic insert 22 selected and the weight and gait of the user. This is represented in FIG. 6a, and is referred to as a plantar flexed condition.

Figure 6B:
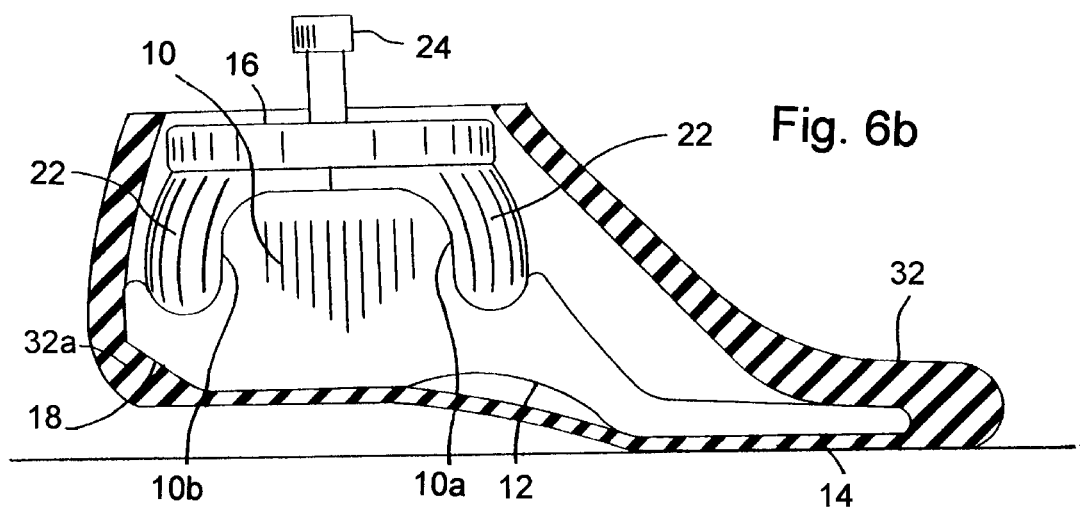
FIG. 6b is a side view showing the foot in a mid stance condition. The cosmetic foot shell is shown in section.

As the step continues the top 16 inclusive of the ball 20, the collar 30 and the attach bolt 24(see FIG. 3 & 4) rotates about the lateral axis until the prosthetic limb (not shown) is vertical and the top 16 is horizontal to the ground. The compression of the elastic insert 22 in the posterior cavity 10b, is relieved. This is the position found in FIG. 6b, and is referred to as a mid stance condition. In this condition neither of the elastic inserts is under compression and the keel 10 bears the load of the user vertically.

Figure 6C:
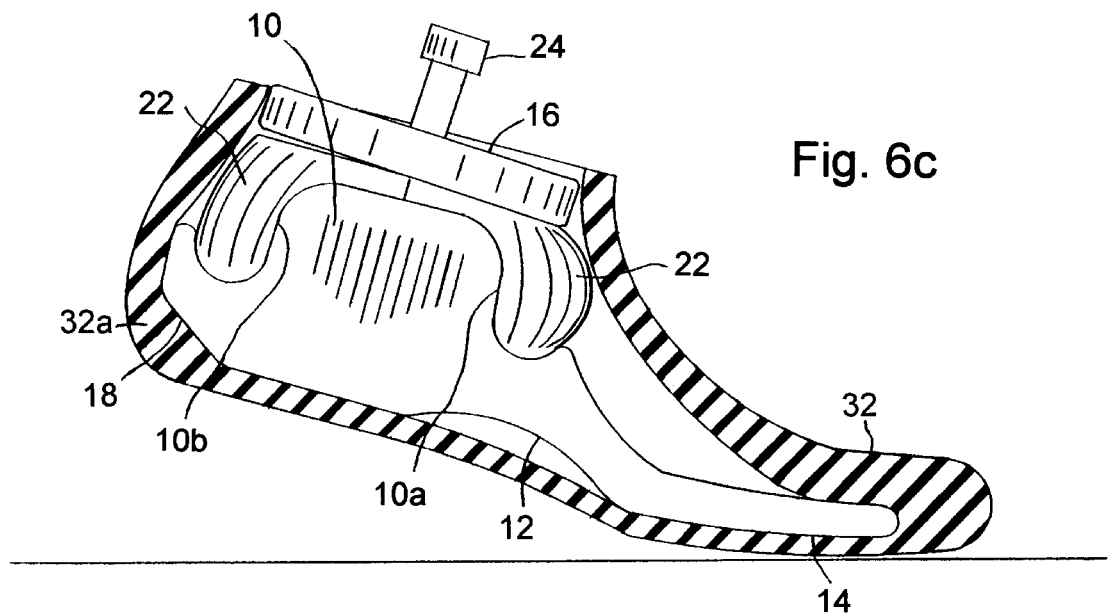
FIG. 6c is a side view showing the rotation of the joint and compression of the elastic insert in a dorsi-flexion condition. The cosmetic foot shell is shown in section.

As the stride proceeds beyond mid stance the arch 12 and toe 14 start to assume the load, the first reaction is the compression of the thin section of the foot shell 32 material between the toe 14 and the ground. Next the thin section of the toe 14 deflects as more load is applied. The arch area 12 next is "loaded" or deflected. Then the rotation of the keel 10 about the lateral axis begins to compress the elastic insert 22 installed in the anterior cavity 10*a* against the top 16; the speed and degree of rotation is controlled by the selected durometer of the elastic insert 22 installed as well as the weight and gait of the user. When it reaches its maximum degree of rotation as depicted in FIG. 6*c* it is said to be in a dorsiflexed condition.

When the load or weight starts to come off of the foot the resilience of the elastic inserts 22 installed in the anterior cavity 10*a* starts to rotate the ankle back toward a neutral position where neither of the elastic inserts 22 are compressed. The arch 12 and the toe 14 "unload" and return to a non flexed condition. The combination of this loading and unloading of the keel 10 the arch 12, the toe 14 and elastic inserts 22 result in the push commonly refereed to as "energy storage" and return.

Conclusions, Ramifications, and Scope

Accordingly, the reader will see that the Prosthetic foot with ankle of this invention have many advantages over the prior art.

Function: This foot with a resilient arch and toe, and compressible elastic inserts; working in combination with an ankle joint which in turn allows movement simulating the natural motion of the human foot, will give the user the benefit of energy storage and return as well as the comfort of ankle motion.

Simplicity: This foot/ankle allows the user or the fitter the advantage of quick initial fittings, as well as quick simple adjustments.

Low Maintenance: With only 5 parts per assembly and only one moving part, this foot/ankle requires very little maintenance.

Convenience: The user can easily change the gait characteristics without any disassembly of the ankle joint, and no tools or training are required.

Economy: The manufacturing process for this foot/ankle is a relatively inexpensive molding or casting technique which can allow a less costly design than prior art. The material from which this foot/ankle is manufactured is less expensive than the carbon composites used in most other designs.

Although the descriptions above contain many specifications, these should not be construed as limiting the scope of the invention but as merely providing illustrations of some of the presently preferred embodiments of the invention. For example, the ball and socket could be molded or casted in some other shape, or the orientation of the joint could be rotated so that the ball could be casted as part of the keel and the socket casted as part of the top.

Thus the scope of this invention should be determined by the appended claims and their legal equivalents, rather than by the examples given.

What is claimed is:

1. An energy storing prosthesis comprising:
    a prosthetic foot member including integral heel and toe sections and defining a socket of elliptical shape along a frontal plane therethrough and of circular shape along a sagittal plane therethrough; and
    a prosthetic ankle member including an ellipsoidal ball positioned within and substantially conforming to said socket to thereby form an ankle joint.

2. The energy storing prosthesis of claim 1, further comprising front and rear elastic inserts disposed between respective portions of said foot member and said ankle member.

3. The energy storing prosthesis of claim 2, wherein said prosthesis is adapted to facilitate replacement of said inserts.

* * * * *